United States Patent [19]

Harris et al.

[11] 4,191,922
[45] Mar. 4, 1980

[54] ELECTROMAGNETIC FLAW DETECTION SYSTEM AND METHOD INCORPORATING IMPROVED AUTOMATIC COIL ERROR SIGNAL COMPENSATION

[75] Inventors: Richard M. Harris, Mentor; Wilbert J. Janos, North Ridgeville, both of Ohio

[73] Assignee: Republic Steel Corporation, Cleveland, Ohio

[21] Appl. No.: 886,392

[22] Filed: Mar. 14, 1978

[51] Int. Cl.² ............................................. G01R 33/12
[52] U.S. Cl. .................................... 324/225; 324/233; 324/238; 324/241
[58] Field of Search ............... 324/200, 219, 220, 225, 324/226, 228, 233, 234, 238, 239–243

[56] References Cited

U.S. PATENT DOCUMENTS

| | | | |
|---|---|---|---|
| 3,278,839 | 10/1966 | Wells et al. | 324/234 |
| 3,566,258 | 2/1971 | Mori et al. | 324/233 |
| 3,701,941 | 10/1972 | Bantz et al. | 324/238 |
| 3,763,424 | 10/1973 | Bennett, Jr. et al. | 324/226 |
| 3,900,793 | 8/1975 | Mansson | 324/233 |
| 3,916,301 | 10/1975 | Vild et al. | 324/226 |
| 4,006,407 | 2/1977 | Flaherty et al. | 324/233 |

FOREIGN PATENT DOCUMENTS 1196382 6/1970 United Kingdom .

Primary Examiner—Robert J. Corcoran
Attorney, Agent, or Firm—Watts, Hoffmann, Fisher & Heinke Co.

[57] ABSTRACT

An electromagnetic flaw detection system and method having automatic dynamic error balancing is disclosed.

The system includes means for producing an alternating electromagnetic field and for passing a metallic workpiece to be tested along a path through the field. A differential detection coil is disposed in the field near the workpiece path. The coil responds to nonuniformities in the field caused by workpiece flaws, such as voids, to produce flaw indications. Detection circuitry actuates alarm apparatus in response to the flaw indications to further indicate need for corrective action.

Automatic balancing circuitry compensates for an error signal, which the differential coil generates due to minute undesired assymmetries in the coil's mechanical structure. The balancing circuitry includes means for generating a reference signal. The reference signal is continually adjusted, in response to characteristics of the error signal, to exactly counterbalance the error signal in phase and amplitude. The coil's total output, including the error, and the adjusted reference signal, are summed at a location electrically separate from the coil to provide a flaw detection coil output in which the error is completely nulled out.

15 Claims, 4 Drawing Figures

ELECTROMAGNETIC FLAW DETECTION SYSTEM AND METHOD INCORPORATING IMPROVED AUTOMATIC COIL ERROR SIGNAL COMPENSATION

BACKGROUND OF THE INVENTION

1. Field of the Invention

This invention relates to electromagnetic flaw detection techniques and systems for use on metallic workpieces. Specifically, it relates to circuitry for balancing out unwanted error signals produced by flaw sensing elements of such systems.

2. Description of the Prior Art

Various methods and apparatus have been proposed for enabling the nondestructive testing of elongated metal workpieces such as wires, rods, tubing, pipes and billets. These proposals generally enabled detection of seams, voids and other defects which could be troublesome in a final product made from such workpieces.

In the past, a common method of inspecting such workpieces for defects was by visual observation. In spite of the utmost care, a mill inspector often overlooked seams or other defects. Moreover, visual inspection did not dependably determine the depth of a defect. Another problem with visual inspection is that it is dependent on human judgement and vision, both of which are subject to change, even in the case of the same inspector.

These problems have been overcome to a considerable extent by the use of automatic nondestructive testing equipment. Generally, such equipment operates by producing an electromagnetic exciting field in the region of the workpiece, and by moving a workpiece along a path through the field relative to a sensing element, such as a detection coil, also positioned in the field.

Such systems produced at the terminals of the coil a signal in response to nonuniformities in the electromagnetic field, which nonuniformities were in turn caused by inhomogeneities in the workpiece material passing by the coil.

Detection coils have been provided such that they either encircle the workpiece path of movement, or are placed adjacent that path. The signals produced by the detection coil actuated other apparatus which signalled the need for corrective action with respect to the flawed workpiece.

Where ferromagnetic workpieces are tested, it is known to provide a saturation circuit having a saturation coil connected to a source of D.C. voltage. The saturation coil induces a large D.C. magnetic field in the workpiece. The purpose of this saturation field is to reduce the magnetic permeability of the workpiece to near unity, to enable currents generated in the workpiece by the exciting field to penetrate the workpiece surface, and also to cancel out magnetic variations in the workpieces which might affect test results.

In eddy current testing, it is also known to use a separate exciter circuit including an exciter coil for inducing an alternating electromagnetic field in the workpiece. The exciter coil has either encircled, or been placed adjacent to, the workpiece path. In systems with a separate exciter circuit, the detection circuit has a separate detection coil also positioned near the workpiece path. The detector is connected to other circuit components for generating flaw indicating signals in response to voltage generated in the detection coil.

The flaw sensing coil has frequently been of the differential type. A differential coil consists of two series connected windings, substantially identical but wound with opposing magnetic polarity, longitudinally displaced and aligned along a common axis. The advantage of the differential coil is that it is not sensitive to even large magnitude electromagnetic fields, when those magnetic fields are substantially uniform over the entire region occupied by the coil. The differential coil produces no output in response to even large ambient steady state electromagnetic fields passing through it, such as from the exciter circuit. Rather, the differential coil responds only to localized nonuniformity in the field, such as results from the presence of workpiece flaws proximate the differential coil, when the flaws are geometrically "off center" with respect to the coil's length.

Another advantage of the differential coil is that a relatively small flaw, introducing a relatively small nonuniformity of the field induced in the workpiece, produces an output voltage across the differential coil which is more easily detected than that produced by a coil wound only in one direction. The coil wound only in one direction, when excited by an A.C. field, will constantly produce an output which is of relatively large magnitude. The presence of a small flaw in a workpiece moving with respect to such a detection coil alters the steady state signal by only a fractional amount. It is more difficult to detect small changes in a relatively large signal than to detect merely the presence of a signal, even though that signal may be small, where there was no signal before.

A problem with the use of differential coils is that most differential coils, however carefully constructed, are slightly unbalanced. They are unbalanced because the two oppositely wound portions frequently do not have identical configurations. In the presence of a uniform field, even a minutely unbalanced differential coil will produce a small but undesirable error output. The error output is undesirable in instances such as flaw testing because it is desired that the coil produce no output at all in the presence of an unflawed workpiece. The error output can sometimes be mistaken for a sign of a flaw, even though the workpiece may be perfect.

In order to obtain a proper zero output from a differential coil in the presence of an unflawed workpiece, balancing circuits have been devised to compensate for the imbalance which can result when even an unflawed workpiece is placed proximate the coil. In preparing such a system for operation, the balancing circuit is adjusted to achieve a zero output with an unflawed workpiece in proximity to the coil.

It is known to provide balancing circuitry in which the error signal produced across the entire differential coil is combined with an independently derived reference signal. In one form, the combination of signals is by a summing circuit. The reference signal is derived by adjusting the phase of a signal, having frequency equal to that of the field and of the error signal, to be precisely opposite the phase of the error signal. Additionally, the amplitude of the reference signal is adjusted to be equal to that of the error signal.

The previously used balancing circuits for differential coils have been manually operated. Manually operable controls have been used to adjust separately the amplitude and phase angle of the balancing signal.

Such balancing circuitry incorporated into a prior art flaw detection system is illustrated and described in U.S. Pat. No. 3,916,301, issued Oct. 28, 1975 for MAGNETIC FLAW DETECTION APPARATUS by Vild et al, which is expressly incorporated by reference here.

During normal testing conditions the sensing coil error signal may shift, thus requiring frequent readjustment of the manual controls to rebalance the test system. The test system must be monitored and rebalanced as necessary by a test operator.

While it is sometimes possible to maintain effective balancing by the use of the previously described circuitry and a diligent operator, there are obvious disadvantages attendant on this technique. The operator's time required can be costly, and his diligence must be depended upon to maintain effective and accurate testing conditions. Even a diligent operator can sometimes make mistakes in the frequent readjustments which are necessary. All these factors can reduce testing accuracy and increase operating cost.

It is known, in eddy current flaw detection apparatus, to employ a form of automatic balancing in an eddy current flaw detection apparatus utilizing a bridge detection circuit including two detection coils. This proposal involves circuitry for generating a supplemental signal to maintain the bridge in balance when an unflawed workpiece is near the detection coils.

Two alternating mutually orthogonal signals are produced. The two signals are automatically amplitude controlled such that the vector sum of their outputs constitutes a signal which will balance the bridge.

The effective dynamic range of the above described bridge correction circuitry is considerably limited, substantially circumscribing its ability to cope with error signals of widely varying phase and amplitude.

Since error signals can vary considerably in amplitude and phase angle where a differential coil is used, it is desirable that an automatic balancing system have dynamic range which is as great as possible.

Another disadvantage of this prior art proposal stems from the fact that the supplementary signal is injected directly into the detection coils. Such a technique can introduce undesirable transients which can cause spurious flaw indications.

SUMMARY OF THE INVENTION

Disadvantages of the prior art as described above are ameliorated by electromagnetic flaw detection utilizing a differential coil and special automatic circuitry for continually balancing out error signals resulting from coil imperfections.

Apparatus in accordance with this invention includes circuitry for exciting an electromagnetic field, and a differential coil positioned in the region of the field for flaw sensing. The differential coil, because of unavoidable minor manufacturing imprecision, is susceptible of producing an error signal in response to the field. The apparatus further includes mechanical apparatus for moving a metallic workpiece through the field relative to the differential coil. This causes the coil to produce an output in response to the passage of a workpiece flaw, such as a void, through the region of the coil. Detection circuitry is coupled for detecting the coil output, which electrically indicates the presence of passing flaws.

Automatic balancing circuitry is provided. The automatic balancing circuitry nulls out the error signal in response to monitored characteristics of the error signal itself. The balancing circuitry operates substantially continually.

This feedback control circuitry can be simply and economically embodied in solid state form, for inexpensive and durable construction, low power requirements, and long life.

The apparatus of the invention thus provides an automatic and continuous means for monitoring and cancelling out a single differential coil's error signal without the necessity to rely on the imprecision and expense of operator intervention. Since the automatic balancing circuit operates on a continual basis, difficulties due to system drift, which might change the error signal, are minimized.

In accordance with one aspect of the invention, the balancing circuitry comprises means for generating a reference signal, and further circuitry for adjusting the reference signal to have opposite phase and equal amplitude relative to the error signal. The adjusting circuitry operates in response to the error signal itself. The system nulls out the error signal by summing the total signal output from the differential coil (which includes the error) with the adjusted reference signal. This subtracts out the error signal, leaving only the flaw indicating signals from the coil.

According to a more specific aspect of the invention, the reference adjusting circuitry includes means for phase shifting the reference signal and a phase comparator responsive to both the summed and the phase shifted signals for maintaining the phase of the adjusted reference signal opposite that of the error signal. The reference adjusting circuitry also includes attenuating circuitry for adjusting the amplitude of the phase shifted reference signal, and an amplitude comparator which responds to the summed output signal and the phase shifted signal for maintaining the amplitude of the phase shifted signal equal to that of the error signal.

The automatic balancing system of this invention has dynamic range far superior to that of known prior art. For example, the balancing circuitry can effectively and accurately null error signals having amplitudes as low as one millivolt, and as high as 25 volts. Thus, the inventive apparatus can compensate for error signals over an extremely wide amplitude range. Another aspect of the invention is that the balancing circuitry can effectively compensate for error signals regardless of their relative phase angle. This further enhances the dynamic range and versatility of the system.

A further feature involves the combining of the adjusted reference signal with the coil output signal in circuitry which is electrically segragated from the differential coil itself. This electrical separation alleviates any need, such as in the prior art, for injecting the compensating signal directly into the coil itself, and eliminates the likelihood of thereby producing undesirable transients.

The invention described herein will be understood in more detail by reference to the following detailed description, and the drawings, in which:

DESCRIPTION OR THE DRAWINGS

DESCRIPTION OF THE PREFERRED EMBODIMENT

Figure 1:
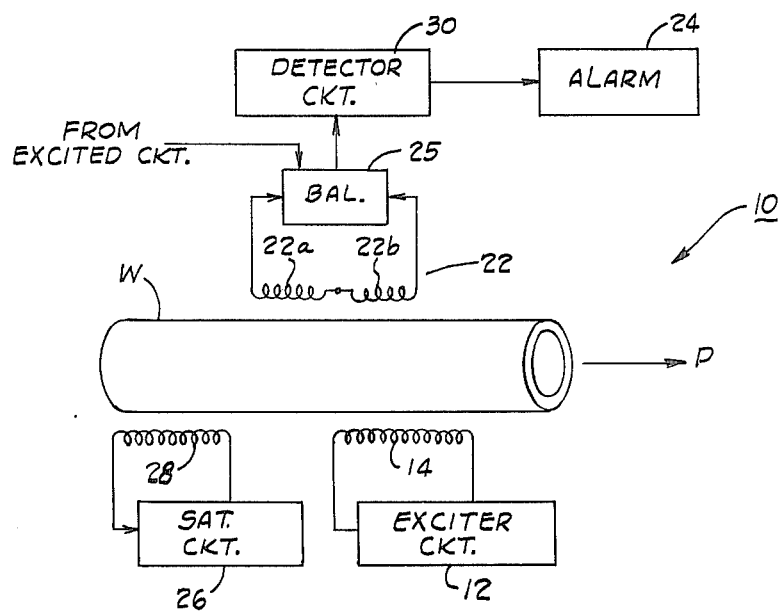
FIG. 1 illustrates a system incorporating the present invention, in both block and graphical form.

A system 10 for detecting flaws in workpieces is shown in FIG. 1. A typical workpiece W is illustrated in FIG. 1 moving relative to the system 10 along a path generally indicated by the arrow P. The workpiece W is preferably an elongated metallic item, such as a portion of rod, wire or pipe.

The system 10 includes an exciter circuit 12 connected to an exciter coil 14 for generating an alternating electromagnetic exciting field in the region of the workpiece W. Detection circuitry 30 responds to a detection coil 22 positioned near the path P for sensing variations in the electromagnetic field which occur in response to the presence of voids or other flaws in the passing workpiece W. The coil 22 produces a voltage output when a flaw passes by. The detection circuit 30 produces flaw indicating signals in response to the voltage-indicated sensing of such workpiece flaws by the coil 22. The flaw indicating signals actuate an alarm 24 to produce signal indicating the presence of a flaw in the workpiece W and the consequent need for corrective action.

A saturator circuit 26 connected to a saturator coil 28 generates a D.C. magnetic field which magnetically saturates the workpiece. The saturation field causes the magnetic permeability of ferromagnetic workpieces to approach unity, to facilitate eddy currents, which are caused by and interact with the alternating exciting fields in the indication of the flaws, for penetrating the "skin" region of the workpiece and to cancel out magnetic nonuniformities in the workpieces.

The exciter circuit 12 preferably includes an oscillator and an amplifier. The oscillator is preferably a suitable variable frequency oscillator for generating a substantially sinusoidal output signal having a frequency adjustable between 400 Hz. and 20,000 Hz. The lower frequencies, which cause deep penetration of eddy currents, are used to test thick walled workpieces, while higher frequencies, having a better signal to noise ratio, but causing less deep penetration, are more suitable for identifying small flaws and in thinner walled workpieces. The amplifier is connected to the output of the oscillator and is an operational amplifier of known design, such as a type 440.

The exciter coil 14 is driven by about a 50 volt alternating signal from the exciter circuit. Although the exciter coil is shown in FIG. 1 as being adjacent the path P of the workpiece W, it is to be understood that the exciter coil 14 may alternatively encircle the workpiece W as it moves along the path P.

The detection coil 22 is preferably a differential coil. Such a differential coil comprises two winding segments 22a, 22b, connected in series and in close proximity to one another. The segments 22a, 22b are wound such that they have opposing electromagnetic polarity. The detection coil 22 ideally produces no output in response to a substantially uniform alternating ambient electromagnetic field passing through both portions. The detection coil, then, ideally produces a signal only in response to nonuniformity in the electromagnetic field which causes the induced voltages in the portions 22a, 22b to be unequal, giving a net output voltage across the whole coil. Such a condition prevails when a workpiece flaw, such as a void, is positioned near, but longitudinally off center, with respect to the two portions of the coil 22.

The signal produced across the entire detection coil 22 has the same frequency as that produced by the exciting current, but varies in amplitude and phase in response to the differing nature of workpiece flaws moving past the detector coil 22. The frequency of the signal produced by the detection coil is known as the "carrier" frequency.

Differential detector coils, in practice, commonly produce an error voltage even in the presence of a uniform field. This error voltage constitutes an output across the detection coil 22 even when the detection coil 22 is positioned adjacent or encircles an unflawed workpiece. This susceptibility to error signal production results from minute assymetry in the winding segments 22a, 22b. Such differences result because of mechanical imperfections which virtually always occur in the course of manufacturing differential coils.

A system constructed generally in accordance with the foregoing description and generally incorporating its components is described in the above referenced U.S. Pat. No. 3,916,301 to Vild et al.

Balancing circuitry 25 is coupled to the coil, and to the detection and exciter circuitry, for nulling out the error signals to prevent the spurious indication of flaws.

Figure 2:
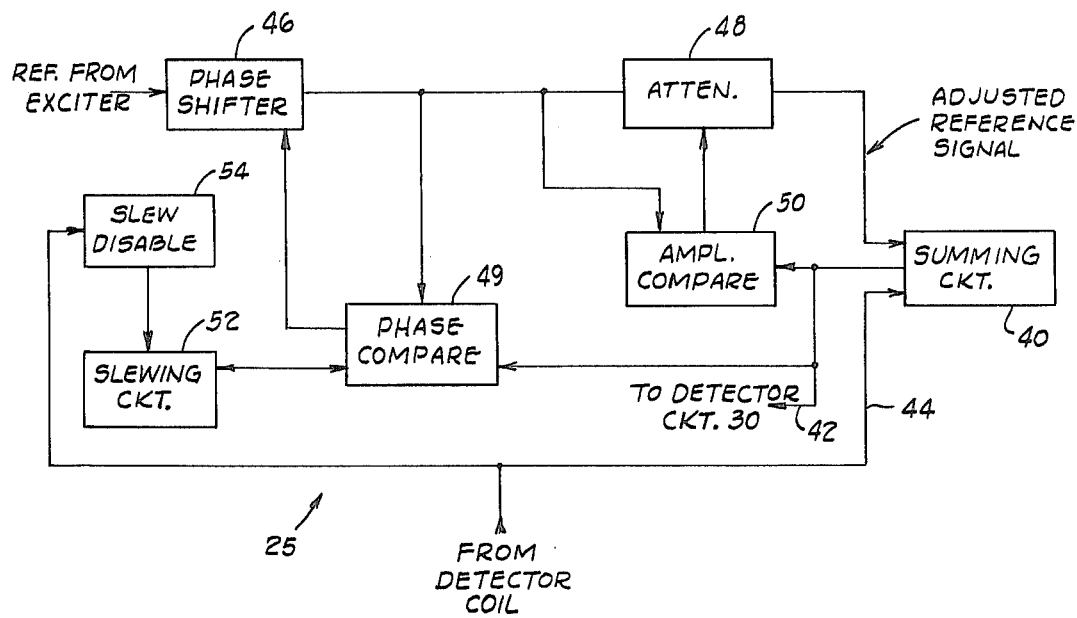
FIG. 2 is a detailed block diagram of a portion of the system of FIG. 1.

FIG. 2 illustrates the components of the balancing circuitry 25 in detailed block form.

The output of the balancing circuitry to the detector circuitry 30 is from a summing circuit 40, over a lead 42. The signal appearing at the lead 42 includes the voltage signals indicating flaws, produced by the detector coil 22, an error signal, and a compensatory nulling signal which exactly offsets the error signal in phase angle and amplitude.

More specifically, the compensatory nulling signal is an adjusted reference signal derived from, and having the same frequency as, the field excitation signal. The adjusted reference signal is input to the summing circuitry 40, along with the output signal from the detector coil 22. The detector coil output signal, appearing on a lead 44, includes both the voltage signals from the detection coil which indicate the existence of workpiece flaws, and any error signal. The summing circuitry subtracts the adjusted reference signals from the composite signal at the lead 44 thereby deriving its output signal in which the error signal is completely nulled.

The adjusted reference signal is produced by appropriately phase shifting and attenuating a reference signal derived in known fashion from the excitation circuitry. A phase shifter 46 and attenuator 48 are series coupled to receive and process the reference signal for this purpose.

The signal from the excitation circuitry is a sinusoidal alternating signal having the carrier frequency, and has an amplitude of about 10 volts peak to peak.

The phase shifter adjusts the phase of the reference signal such that it is directly opposite that of the error signal. The phase shifter performs this function in response to a phase comparator circuit 49. The phase comparator circuit responds to the phase shifted signal and to the output from the summing circuit 40 to maintain the phase shifted signal in its diametrically opposed phase with respect to the error signal.

An amplitude comparator 50 responds to the phase shifted signal and to the summed output signal to adjust the attenuator 48 to maintain equality of amplitude between the adjusted reference signal and the error signal.

A slewing circuit 52 responds to the output signal from the phase comparator 49 to cause the phase comparator to slew, or track, when needed (as explained below) until the system phase shifts 360°, to allow the system to balance in an advantageous region of the phase range. A slewing disable circuit 54 serves to disable the slewing circuit temporarily whenever the output signal from the detector coil 22 drops below a level required for proper operation of the slewing circuit, i.e., about 1 millivolt.

Figure 3:
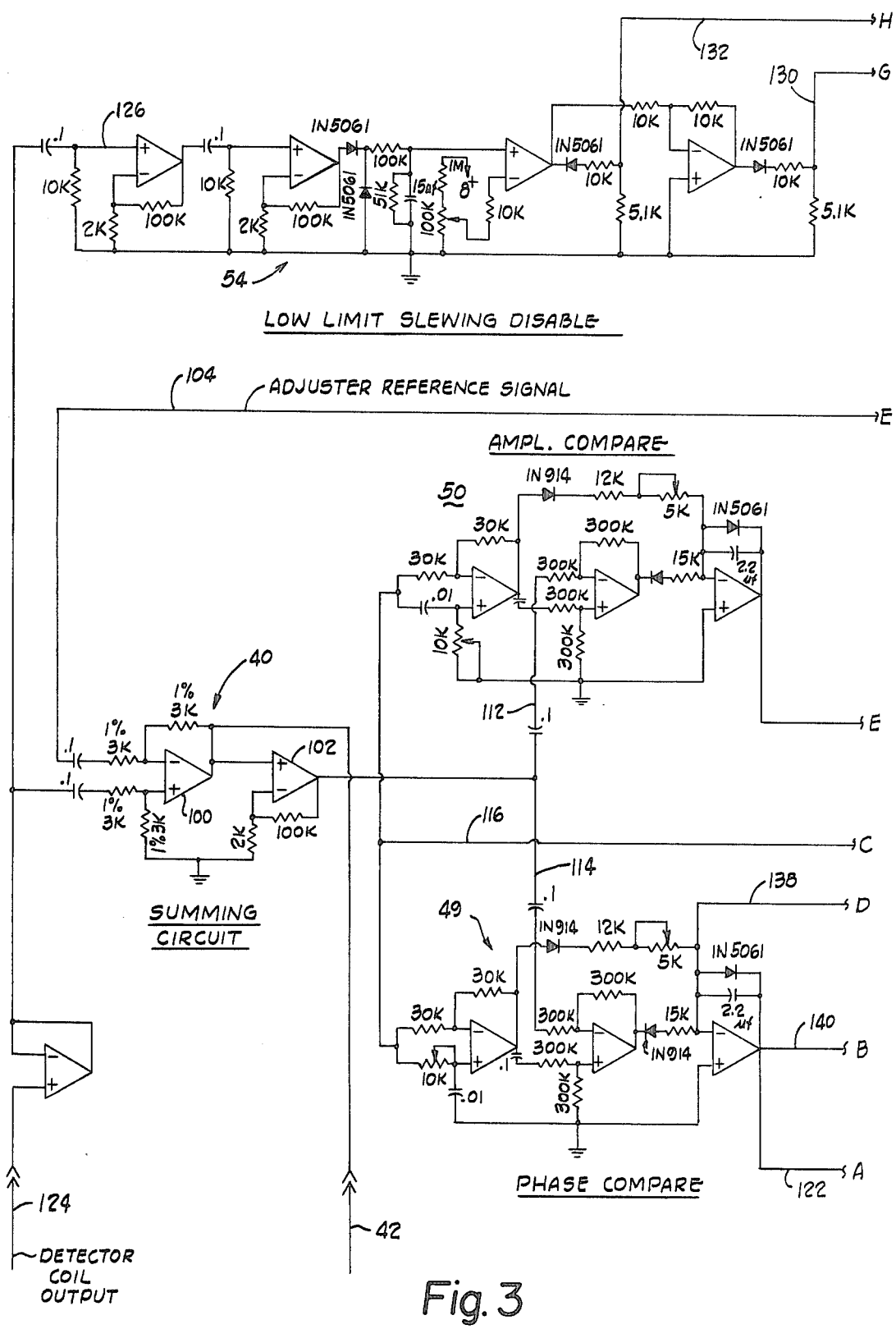
FIGS. 3 and 4 are schematic drawings of portions of the system illustrated in FIG. 2.
Figure 4:
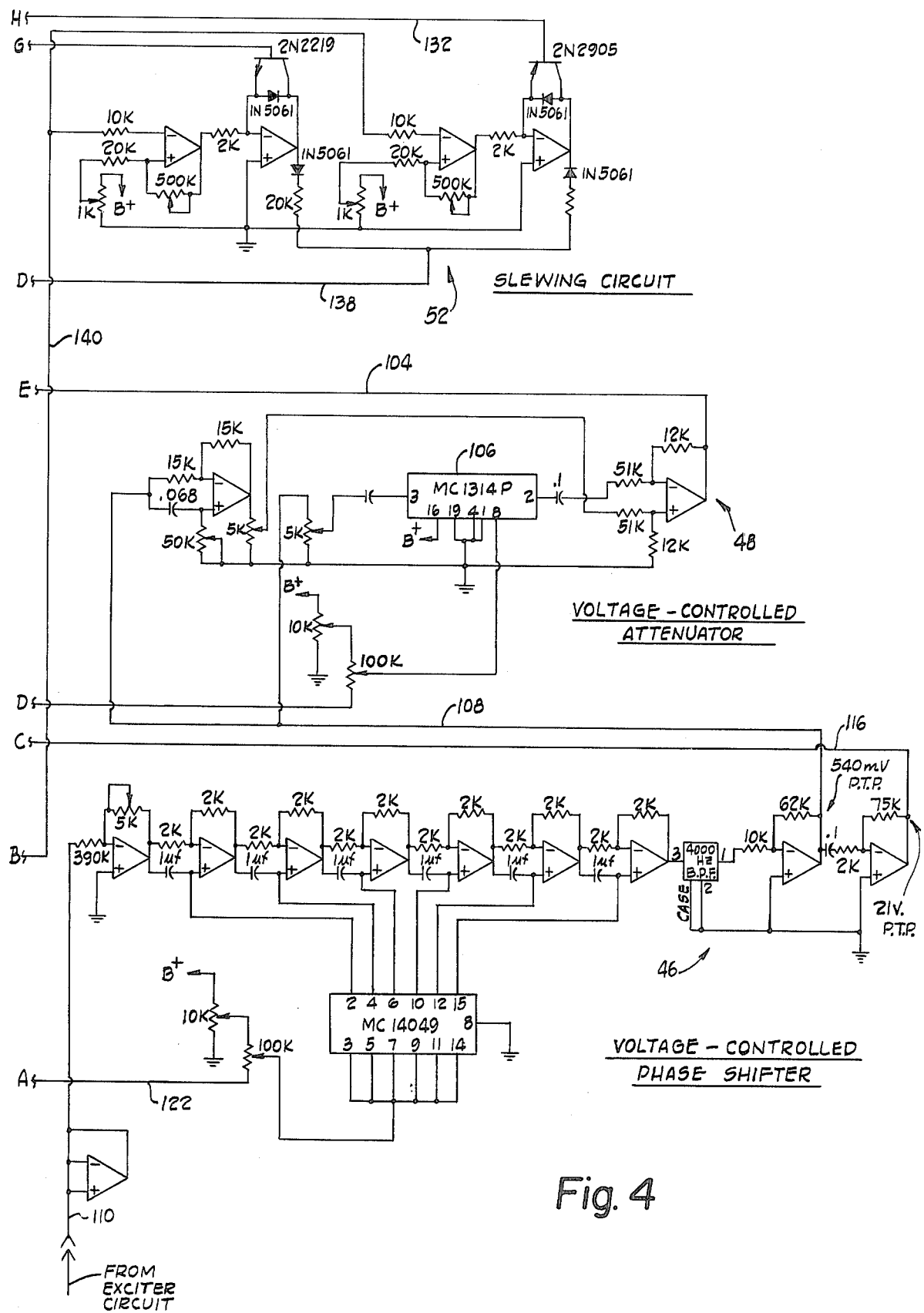

The components of the balancing circuitry 25 are illustrated in schematic form in FIGS. 3 and 4.

The summing circuitry 40 is shown in detail in FIG. 3. This circuit employs a precision differential amplifier 100 having unity gain so that the output of this amplifier is a signal including the flaw sensing signal which is not undesirably influenced by the amplifier, to avoid need for sensitivity adjustment of system circuitry. A secondary loop gain stage 102 is also provided to amplify detectable variances for effective use by the amplitude and phase comparator circuits 50, 49.

The output of the summing circuitry 40 appearing on the lead 42 is directed to the detection circuitry 30. The detection circuitry 30 operates upon this output signal in known fashion, as illustrated and described in the incorporated patent reference.

The adjusted reference signal is fed to one input of the summing circuitry 40 over a lead 104 which extends, by way of terminals indicated as E, from an output of the attenuator circuitry 48 (see FIG. 4).

The attenuator circuit is designed for linear voltage to amplitude response. Since the lower end of the linear region of the voltage-amplitude function is in practice not zero, this lower limit amplitude is differentially summed with a matching signal to artificially form a zero point. The principal component of the attenuator circuitry 48 is an integrated circuit chip designated by reference character 106 and by its chip number, MC 1314P.

The phase shifted reference signal is directed from the output of phase shifting circuitry 46 to an input of the attenuator circuitry 48 over a lead 108. The phase shifting circuitry 46 is designed for linear voltage to phase response. This is achieved by employing several phase shift sections, each section providing only a small degree of phase shift. The circuit chip designated in FIG. 4 as MC 14049 is a digital inverter buffer, but is connected in such a way as to use its field effect transistors as voltage controlled resistors.

The reference signal from the exciter circuit is impressed on an input of the phase shifting circuitry 46 by way of a lead 110 (FIG. 4).

The attenuator circuitry 48 and the phase shifter 46 are controlled by respective amplitude and phase comparator circuits 50, 49. The amplitude comparator circuit 50 receives as one input a signal from the output of the summing circuitry 40 over a lead 112 (FIG. 3). A corresponding input is directed by a lead 114 to an input of the phase comparator circuitry.

The amplitude comparator circuitry 50 also receives an input from the output of the phase shifting circuitry 46 representing the phase angle of the phase shifted reference signal. This input is transmitted over a lead 116. (FIG. 3).

The phase comparator circuitry 49 operates in response to the signal from the output of the summing circuitry 40, and to another input representing the phase angle of the phase shifted reference signal at the output of the phase shifter 46, to control the phase shifter 46 in a closed loop feedback manner to maintain the phase of the phase shifted signal opposite that of the error signal. The output from the phase shifting circuitry 46 is transmitted over the lead 116, in a manner similar to that with respect to the amplitude comparator. The output of the phase comparator circuitry 49, for controlling the phase shifter circuitry 46, is delivered to the phase shifter 46 over a lead 122.

The comparator circuits are composed of a phase shifter, a differential amplifier and a summing integrator. The phase shifter is adjusted to sensitize the comparator to either phase or amplitude signals, as appropriate. A unique quality of the disclosed and illustrated circuit besign allows the comparators to ignore unwanted reference amplitude variations from the phase shifter while still detecting error nulling information.

The output from the differential detector coil, carrying both flaw indicating and error signals, appears upon a lead 124 (FIG. 3) and is input to one input of the summing circuitry and to an input 126 of a low limit slewing disable switch circuitry. The output of the slewing disable circuit is transmitted to inputs of the slewing circuitry 52 (FIG. 4) over a lead 130 and by way of another lead 132. The slewing circuit output is carried over a lead 138 to the phase comparator.

The slewing circuit uses two comparators with hysteresis to detect the voltage extreme "latching" points of the phase comparator output, beyond which that circuit cannot operate properly. When such an extreme is encountered, (e.g. about 1 volt and 14 volts, output, in practice) the phase comparator is caused to "slew", or track, until system phase has shifted 360 degrees. This facilitates balancing in an advantageous range of phase, in which the circuitry is most effective.

The slewing disable circuit includes two amplifiers, a comparator, and an inverter. It disables the slewing circuit when its input amplitude falls below the level required for proper slewing circuit operation, (i.e., about 1 millivolt). A pair of switching transistors disables the slewing circuit by shorting out its feedback elements.

It is to be understood that this disclosure is intended to be illustrative, rather than exhaustive, of the present inventive subject matter. Those of ordinary skill can make additions and changes thereto without departing from the substance, spirit and scope of the invention, as expressed in the following claims:

What is claimed is:

1. An electromagnetic flaw detection system comprising:
   (a) circuitry for exciting an electromagnetic field;
   (b) circuitry including a coil in the region of the field and susceptible of producing an error signal when in the field, said error signal having a phase angle with respect to a reference;
   (c) apparatus for moving a metallic workpiece in the field relative to the coil, for causing the coil to produce an output in response to the passage of a flawed workpiece;
   (d) circuitry coupled to the coil for detecting the coil output, and
   (e) balancing circuitry responsive to the error signal including circuitry for automatically nulling error signals having a phase angle ranging over 360° with respect to the exciting field.

2. The system of claim 1, wherein said balancing circuitry comprises:

(a) circuitry for generating a reference signal;
(b) circuitry responsive to the error signal for adjusting the reference signal continually to have opposite phase and equal amplitude relative to said error signal, and
(c) summing circuitry for combining said error and said adjusted reference signals.

3. The system of claim 2, wherein said reference adjusting circuitry comprises:
   (a) circuitry for phase shifting said reference signal;
   (b) a phase comparator responsive to the relative phases of said combined and said phase shifted reference signals for regulating the phase shifter for maintaining the phase of said phase shifted reference signal opposite that of said error signal;
   (c) circuitry for attenuating said phase shifted reference signal, and
   (d) an amplitude comparator responsive to said combined and phase shifted signals for controlling the attenuator for maintaining the amplitude of the phase shifted and attenuated signal equal to that of said error signal.

4. The system of claim 2, wherein said summing circuitry comprises:
   a precision differential amplifier having a first stage having substantially unity gain, and a second stage in series with said first state.

5. The system of claim 3, wherein said phase shifter comprises:
   a plurality of series connected phase shift sections each including circuitry for providing an amount of phase shift, the total phase shift of the phase shifter being the sum of the phase shifts of the respective series connected phase shift sections.

6. The system of claim 3, further comprising:
   slewing circuitry coupled to said phase comparator for causing the comparator to track its phase shift in response to the phase shifter reaching an extreme point of its phase comparator output range.

7. The system of claim 6, further comprising:
   circuitry for disabling said slewing circuitry in response to said error signal failing to equal or exceed a predetermined amplitude.

8. A method of electromagnetic flaw detection utilizing an exciting field and a detection coil having susceptibility of producing an error signal of any phase relative to a reference in absence of a flaw, said method comprising the steps of:
   (a) generating an electromagnetic field;
   (b) moving a metallic workpiece through the field;
   (c) producing workpiece flaw indicating signals by the use of the coil in the field;
   (d) detecting the flaw indicating signals; and
   (e) automatically nulling the error signal over a 360° phase angle range in response to the existence and characteristics of said error signal by producing a nulling signal having a phase opposing that of the error signal, and an amplitude equal to that of the error signal.

9. The method of claim 8, wherein said nulling step comprises:
   (a) deriving a reference signal;
   (b) adjusting said reference signal in response to error signal characteristics, and
   (c) summing the error signal and said adjusted reference signal.

10. An electromagnetic flaw detection system comprising:
    (a) circuitry for producing an electromagnetic field;
    (b) a flaw sensing coil disposed substantially in the field, and responsive to said disposition for producing flaw indicating signals, said coil being susceptible of producing an undesirable error signal in addition to said flaw indicating signal;
    (c) apparatus for causing relative movement between a metallic workpiece in the field and the flaw sensing coil;
    (d) circuitry for detecting the flaw indicating signals, and
    (e) balance circuitry having a dynamic range for compensating automatically for said error signals having substantially any phase angle over a 360° range, and an amplitude in a range of between approximately 1 millivolt and 25 volts.

11. A method of electromagnetic flaw detection utilizing a flaw sensing coil for producing flaw indicating signals in response to an electromagnetic field, said coil also being susceptible of producing an undesirable error signal in addition to the flaw indicating signal, said method comprising the steps of:
    (a) producing an electromagnetic field;
    (b) disposing the coil in the region of the field;
    (c) relatively moving in the field a metallic workpiece with respect to the coil;
    (d) detecting the flaw indicating signals, and
    (e) compensating automatically for said error signals over a 360° phase angle range and an amplitude range of between approximately 1 millivolt and 25 volts.

12. An electromagnetic flaw detection system comprising:
    (a) circuitry for exciting an electromagnetic field;
    (b) circuitry including a coil in the region of the field, the coil being susceptible of producing an undesirable error signal when in the field;
    (c) apparatus for moving a metallic workpiece in the field relative to the coil, for causing the coil to produce an output in response to movement of a flawed workpiece;
    (d) circuitry coupled to the coil for detecting the coil output, and
    (e) balancing circuitry responsive to the error signal for nulling the error signal, said balancing circuitry comprising:
       (i) circuitry for producing a reference signal having a reference phase;
       (ii) circuitry for phase shifting the reference signal;
       (iii) a phase comparator responsive only to signals each having a component already shifted by said phase shifter for operating upon the phase shifter to maintain the phase of said shifted reference signal opposite that of said error signal;
       (iv) circuitry for attenuating said phase shifted reference signal;
       (v) an amplitude comparator responsive only to signals each having a component already adjusted by said attenuator for controlling the attenuator for maintaining the amplitude of the phase shifted and attenuated reference signal equal to that of said error signal, and
       (vi) summing circuitry for combining said error and said adjusted reference signals for nulling the error signal.

13. An electromagnetic flaw detection system comprising:
    (a) circuitry for exciting an electromagnetic field;

(b) circuitry including a coil in the region of the field and susceptible of producing an undesired error signal when in the field;

(c) apparatus for moving a metallic workpiece in the field relative to the coil, for causing the coil to produce an output in response to the movement of a flawed workpiece;

(d) circuitry coupled to the coil for detecting the coil output, and, (e) automatic balance circuitry responsive to the error signal for producing an adjusted reference signal complimentary to the error signal and for nulling the error signal by summing the error signal with the adjusted reference signal, said balancing circuitry including circuitry for producing a single phase reference signal synchronous with the electromagnetic field, and for producing the complementary signal by phase shifting and attenuating in series the single phase reference signal as a whole without separating the reference signal into component portions.

14. An automatic error nulling system for an electromagnetic flaw detection apparatus utilizing a detection coil in an exciting field to produce an output signal indicating flaws in metallic workpieces in the field and proximate the coil, said coil being susceptible of producing an undesirable error signal in addition to flaw indicating signals, said error nulling system comprising:

(a) circuitry for producing a single phase reference signal;

(b) a phase shifter for adjusting the phase of said reference signal;

(c) an attenuator separate from said phase shifter for attenuating said reference signal, and (d) automatic error nulling circuitry responsive to said error signal and coupled to said phase shifter and to said attenuator for automatically adjusting the phase shifter and attenuator to produce a phase shifted and attenuated reference signal complementary to said error signal and for nulling said error signal by the application of said adjusted reference signal.

15. An automatic error balancing system for use in connection with an electromagnetic flaw detection system having means for exciting an electromagnetic field, means for moving a metallic workpiece in the field, and a detection coil in the field for producing an output signal in response to a flaw in the workpiece, said detection coil being susceptible of producing an undesirable error signal in addition to signals indicating workpiece flaws, said automatic error balancing system comprising:

(a) means for producing a reference signal;

(b) a phase shifter for adjusting the phase of the reference signal;

(c) an attenuator for adjusting the amplitude of the reference signal;

(d) circuitry for combining the phase shifted and attenuated reference signal with the total output signal from the detection coil;

(e) a phase detector responsive to the phase shifted reference signal and the combined signal for controlling the phase shifter to adjust the phase of the reference signal opposite that of the error signal, and (f) an amplitude comparator responsive to the phase shifter reference signal and to the combined signal for controlling the attenuator to adjust the amplitude of the reference signal to equal that of said error signal, whereby the error signal component of the output from the detection coil is nulled out.

* * * * *

UNITED STATES PATENT AND TRADEMARK OFFICE
CERTIFICATE OF CORRECTION

PATENT NO. : 4,191,922
DATED : March 4, 1980
INVENTOR(S) : Richard M. Harris and Wilbert J. Janos It is certified that error appears in the above–identified patent and that said Letters Patent are hereby corrected as shown below:

Column 4, line 52, change "segragated" to --segregated--;

Column 8, line 15; change "besign" to --design--;

Column 12, line 31; change "shifter" to --shifted--.

Signed and Sealed this

Eighth Day of July 1980

[SEAL]

Attest:

SIDNEY A. DIAMOND

Attesting Officer

Commissioner of Patents and Trademarks